(12) United States Patent  
Hart

(10) Patent No.: US 10,631,847 B2  
(45) Date of Patent: Apr. 28, 2020

(54) BONE ANCHOR INCLUDING ONLY SUTURE MATERIAL AND DELIVERY DEVICE THEREOF

(71) Applicant: KARL STORZ GmbH & Co. KG, Tuttlingen (DE)

(72) Inventor: Rick Hart, Marco Island, FL (US)

(73) Assignee: KARL STORZ SE & Co. KG, Tuttlingen (DE)

( * ) Notice: Subject to any disclaimer, the term of this patent is extended or adjusted under 35 U.S.C. 154(b) by 427 days.

(21) Appl. No.: 15/603,770

(22) Filed: May 24, 2017

(65) Prior Publication Data

US 2018/0338754 A1    Nov. 29, 2018

(51) Int. Cl.
*A61B 17/04*     (2006.01)
*A61B 17/06*     (2006.01)

(52) U.S. Cl.
CPC .......... *A61B 17/0401* (2013.01); *A61B 17/04* (2013.01); *A61B 17/06166* (2013.01); *A61B 2017/0406* (2013.01); *A61B 2017/0409* (2013.01); *A61B 2017/0414* (2013.01); *A61B 2017/0445* (2013.01); *A61B 2017/0458* (2013.01); *A61B 2017/0464* (2013.01); *A61B 2017/0475* (2013.01); *A61B 2017/06185* (2013.01)

(58) Field of Classification Search
CPC ................ A61B 17/0401; A61B 17/04; A61B 17/06166; A61B 2017/0406; A61B 2017/0409; A61B 2017/0414; A61B 2017/0445; A61B 2017/0458; A61B 2017/0464; A61B 2017/0475; A61B 2017/06185
See application file for complete search history.

(56) References Cited

U.S. PATENT DOCUMENTS 3,123,077 A     3/1964  Alcamo
4,738,255 A *   4/1988  Goble ................ A61B 17/0401
                                            29/243.519
8,273,106 B2    9/2012  Stone et al.
(Continued)

FOREIGN PATENT DOCUMENTS

EP    2 082 692 A2    7/2009
EP    2 430 984 A1    3/2012
(Continued)

OTHER PUBLICATIONS

Extended European Search Report dated Jan. 28, 2019 in corresponding application 18000458.2.
(Continued)

*Primary Examiner* — Erich G Herbermann
(74) *Attorney, Agent, or Firm* — Muncy, Geissler, Olds & Lowe, P.C.

(57) ABSTRACT

A suture anchor includes a tubular anchor body made of suture material, the tubular anchor body having a partially open distal tip and a bore extending through the tubular anchor body to a proximal end of the tubular anchor body and a suture woven from the distal tip and extending through the bore and exiting through the proximal end, the suture forming a suture loop outside of the distal tip. The tubular anchor body is configured such pulling an end of the suture at the proximal end causes the tubular anchor body to collapse.

12 Claims, 14 Drawing Sheets

(56) References Cited

U.S. PATENT DOCUMENTS

| | | |
|---|---|---|
| 8,361,113 B2 | 1/2013 | Stone et al. |
| 8,652,172 B2 | 2/2014 | Denham et al. |
| 8,795,334 B2 | 8/2014 | Astorino et al. |
| 8,986,327 B2 | 3/2015 | Karasic et al. |
| 2004/0133214 A1 | 7/2004 | Kayan |
| 2009/0112232 A1 | 4/2009 | Crainich et al. |
| 2009/0206124 A1 | 8/2009 | Hall et al. |
| 2010/0204791 A1 | 8/2010 | Shfaram et al. |
| 2011/0082471 A1 | 4/2011 | Holcomb et al. |
| 2011/0098727 A1 | 4/2011 | Kaiser et al. |
| 2011/0264141 A1 | 10/2011 | Denham et al. |
| 2012/0172924 A1 | 7/2012 | Allen, IV |
| 2012/0239085 A1 | 9/2012 | Schlotterback et al. |
| 2013/0018416 A1 | 1/2013 | Lombardo et al. |
| 2013/0023930 A1* | 1/2013 | Stone ................ A61B 17/0401 606/232 |
| 2014/0046368 A1 | 2/2014 | Kaiser et al. |
| 2014/0052178 A1 | 2/2014 | Dooney, Jr. |
| 2014/0114330 A1 | 4/2014 | Karasic et al. |
| 2015/0190131 A1 | 7/2015 | Karasic et al. |
| 2015/0320412 A1 | 11/2015 | Karasic et al. |
| 2016/0051246 A1 | 2/2016 | Durando |
| 2016/0157844 A1 | 6/2016 | Guy |
| 2016/0367357 A1 | 12/2016 | Dougherty et al. |
| 2017/0348090 A1 | 12/2017 | Saint et al. |

FOREIGN PATENT DOCUMENTS

| | | |
|---|---|---|
| EP | 2 572 650 A1 | 3/2013 |
| EP | 2 698 128 A1 | 2/2014 |
| EP | 2 698 117 B1 | 4/2016 |
| KR | 20140138125 A | 12/2014 |
| WO | WO2009/111802 A1 | 9/2009 |
| WO | WO 2013/074691 A1 | 5/2013 |
| WO | WO 2016/134102 A2 | 9/2014 |
| WO | WO 2016/029086 A1 | 2/2016 |
| WO | WO 2016/089396 A1 | 6/2016 |

OTHER PUBLICATIONS

Partial European Search Report dated Oct. 10, 2018 in corresponding application EP18000458.
Biomet, "JuggerKnot Soft Anchor," Ad, p. 1.

* cited by examiner

BONE ANCHOR INCLUDING ONLY SUTURE MATERIAL AND DELIVERY DEVICE THEREOF

BACKGROUND OF THE INVENTION

Field of the Invention

The present invention relates to a soft tissue repair device and more particularly to a bone anchor made of only suture material.

Description of the Background Art

Sutures and suture/bone anchors are used for repairing tissue in surgical procedures to secure soft tissue to bone. Specifically, tears in soft tissues such as cartilage, ligament or muscle can be repaired by suturing. Suture anchors are commonly used during the surgical procedure to provide an attachment location for the suture. The suture anchor may be secured into a bone by inserting the anchor into a pre-formed hole in the bone. Typical suture anchors are made from metallic or polymer materials.

For example, U.S. Patent Application Publication No. 2013/0018416 describes a soft suture anchor manufactured from a single, continuous length of suture. The suture includes braided (i.e., multifilament) suture and monofilament suture, as well as metallic or non-metallic filament material.

Furthermore, U.S. Pat. No. 8,273,106 discloses a soft tissue repair device that includes a deformable tubular member having a longitudinal bore extending between first and second ends, and a flexible strand passing through the longitudinal bore of the tubular member. The flexible strand has a first end portion extending outside the first open end and a second portion forming a first loop that passes through the second open end and an intermediate opening between the first and second open ends. Pulling the first end portion of the flexible strand away from the tubular member deforms a portion of the tubular member between the second open end and the intermediate opening into a folded shape forming a soft tissue anchor.

Additionally, U.S. Pat. No. 8,361,113 discloses a method and apparatus for repairing a tear in soft tissue. The method includes positioning a plurality of collapsible tubes around a suture. The collapsible tubes are pushed through soft tissue and orthopedic mesh on opposite sides of a tear in soft tissue. When tension is applied to the suture, the tubes are compressed, which fixes the suture to the soft tissue. The collapsible tubes (anchors) are made from biocompatible materials (e.g., polymers, woven textile, etc.).

In another example, U.S. Pat. No. 8,652,172 discloses an anchor for securing tissue that includes flexible tubular members and a suture member. The anchor is made from biocompatible materials including, for example, polyester, polyethylene, polypropylene, cotton, silk, etc.

Moreover, U.S. Pat. No. 8,795,334 discloses an apparatus including a flexible fixation member and a suture interwoven through a plurality of openings in the fixation member. The fixation member is made from tape, mesh, tube or other malleable or flexible structures.

Finally, U.S. Pat. No. 8,986,327 discloses an assembly including a flexible fixation member, a suture and a delivery device. The flexible fixation member is a flexible or malleable tube and the suture is woven through the fixation member.

Conventional bone anchors, like those described above, involve a foreign material other than the suture that is left behind in the bone. These foreign materials can cause foreign body reactions. Furthermore, if the bone anchor becomes loose and moves into a joint, the bone anchor can cause damage to articular cartilage. Thus, the inventors have discovered that that there is a need for re-attaching soft tissue back to a bone without any materials other than the suture material.

SUMMARY OF THE INVENTION

In view of the foregoing and other exemplary problems, drawbacks, and disadvantages of the conventional methods and structures, an exemplary feature of the present invention is to provide an all-suture based anchor to reattach soft tissue back to bone without any other materials besides suture material.

According to an exemplary embodiment of the invention, a suture anchor includes a tubular anchor body made of suture material, the tubular anchor body having a distal tip and a bore extending through the tubular anchor body to a proximal end of the tubular anchor body and a suture woven from the distal tip and extending through the bore and exiting through the proximal end. The tubular anchor body is configured such that pulling an end of the suture at the proximal end causes the tubular anchor body to become compressed.

According to an exemplary embodiment a suture anchor consists of or is only formed of or is formed primarily of a tubular anchor body made of suture material, the tubular anchor body having a distal tip and a bore extending through the tubular anchor body to a proximal end of the tubular anchor body and a suture woven from the distal tip and extending through the bore and exiting through the proximal end.

According to an exemplary embodiment, a suture anchor delivery device includes a handle assembly and a draw bar assembly. The handle assembly includes a handle portion, a trigger, pivotably attached to the handle portion and a tubular shaft extending through the handle assembly. The draw bar assembly is retractably disposed within the handle assembly. The draw bar assembly includes a draw bar tube extending through the tubular shaft, the draw bar tube having a channel disposed through the draw bar tube configured to receive a suture, a draw bar housing disposed at a first end of the tubular shaft, the draw bar housing having a cutout configured to receive an end of the suture such that the end of the suture wraps around the cutout and a draw bar disposed within the draw bar tube and configured to receive a suture anchor mounted on a tip of the draw bar. Upon actuating the trigger the draw bar assembly is retracted.

According to an exemplary embodiment, a suture delivery system includes a suture anchor, a suture and a delivery device. The suture anchor has a tubular anchor body made of suture material, the tubular anchor body having a distal tip and a bore extending through the tubular anchor body to a proximal end of the tubular anchor body. The suture is woven from the distal tip and extends through the bore and exiting through the proximal end. The delivery device includes a handle assembly and a draw bar assembly. The handle assembly includes a handle portion, a trigger, pivotably attached to the handle portion and a tubular shaft extending through the handle assembly. The draw bar assembly is retractably disposed within the handle assembly. The draw bar assembly includes a draw bar tube extending through the tubular shaft, the draw bar tube having a channel disposed through the draw bar tube configured to receive the suture, a draw bar housing disposed at a first end of the tubular shaft, the draw bar housing having a cutout configured to receive an end of the suture such that the end of the suture wraps around the cutout and a draw bar disposed within the draw bar tube and configured to receive a suture anchor mounted on a tip of the draw bar. Upon actuating the trigger the draw bar assembly is retracted.

The suture-based anchor described above includes a column of suture material with an interwoven smaller suture or sutures to collapse the anchor when the suture is pulled upon. Accordingly, with the anchor described above, no foreign material other than the suture is left behind in the bone.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus, do not limit the present invention, and wherein.

DETAILED DESCRIPTION

Figure 1:
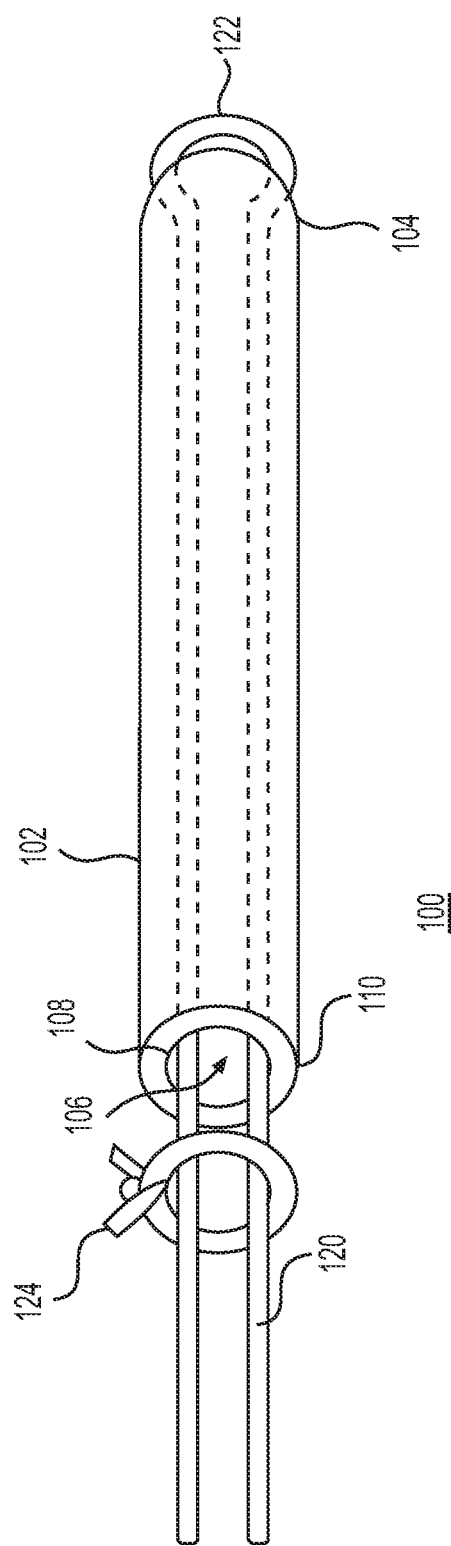
FIG. 1 illustrates a perspective view of a suture anchor 100 according to an exemplary embodiment of the invention.

Referring now to the drawings, and more particularly to FIGS. 1-14, there are shown exemplary embodiments of the method and structures according to the present invention.

FIG. 1 illustrates an all suture based anchor 100 according to certain exemplary embodiments of the present invention. According to an exemplary embodiment of the present invention, the suture based anchor 100 is made entirely of suture material. As is illustrated in FIG. 1, the suture based anchor 100 includes a column 102 made from woven suture material. The column 102 has a closed, distal end 104 at one end of the column. A column-shaped bore 106 extends through the column 102 of the anchor 100. The bore 106 forms an opening 108 at a proximal end 110 of the column 102.

The anchor 100 also includes at least one suture 120 woven into the anchor 100. FIG. 1 illustrates a single suture 120; however, any number of additional sutures may be woven into the anchor 100. As illustrated in FIG. 1, the suture 120 is woven from the distal end 104, through the bore 106 and exits through the opening 108 in the proximal end of the column 102. A loop 122 of suture is formed outside of the distal end 104 of the anchor. The suture loop 122 acts as sling or stop to prevent the suture from pulling thru the distal end 104. This in turn allows the column 100 to collapse when pulled taut. Additionally, as an alternative to the loop 122, knots can be disposed on both ends of the sutures 120. In certain exemplary embodiments of the invention, more than one suture 120 is woven through the bore 106. If more than one suture 120 is provided, then a corresponding number of sutures loop 122 will be formed outside of the distal end 104 of the anchor 100. Finally, a sliding knot 124 is tied an end of the suture. The sliding knot 124 provides friction to prevent the sutures 120 from backing out when the sutures are pulled taut. Thus, the sliding knot 124 prevents the sutures from loosening from the collapsed state, which would cause the anchor construct to straighten and possibly pull out of the hole. Accordingly, the entire anchor 100 is composed of only suture material. Thus, with the all suture based anchor 100, according to certain exemplary embodiments of the present invention, no foreign material other than the suture is left behind in the bone.

Figure 2:
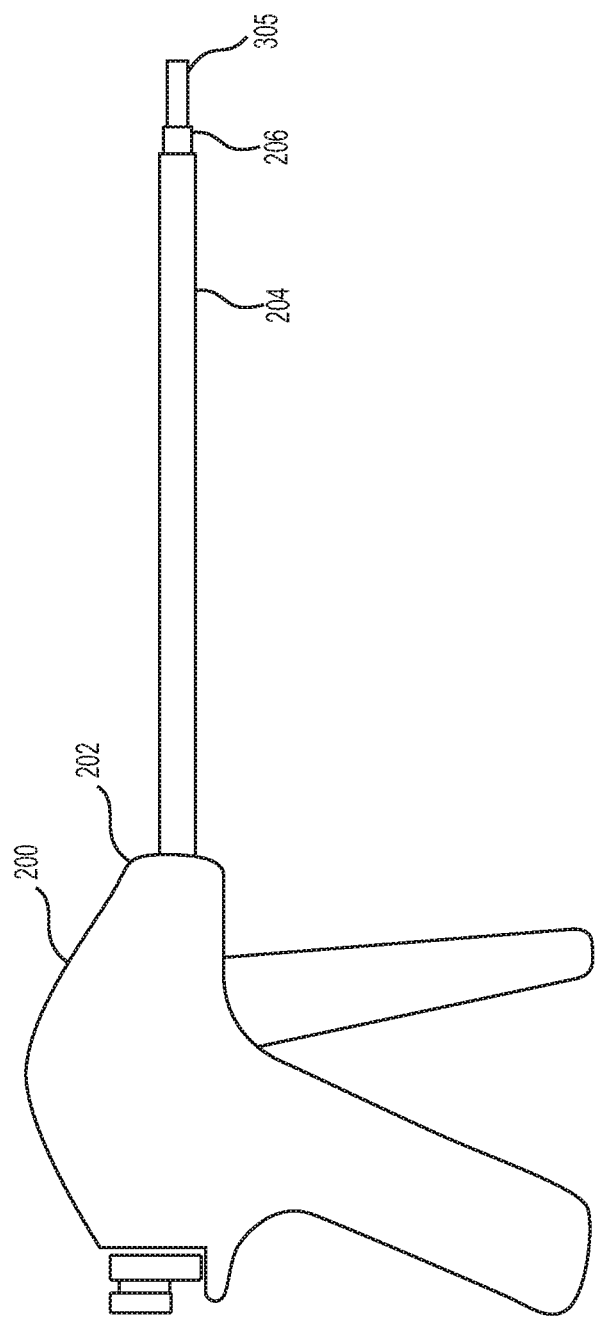
FIG. 2 illustrates a suture anchor delivery device according to an exemplary embodiment of the invention.

FIG. 2 illustrates a suture anchor delivery device 200 according to an exemplary embodiment of the invention. The delivery device 200 includes a housing (handle) portion 202 and an elongate, tubular shaft 204 extending outwardly from the housing portion 202. A shaft tip 206 is disposed at a distal end of the elongate shaft 202.

Figure 3:
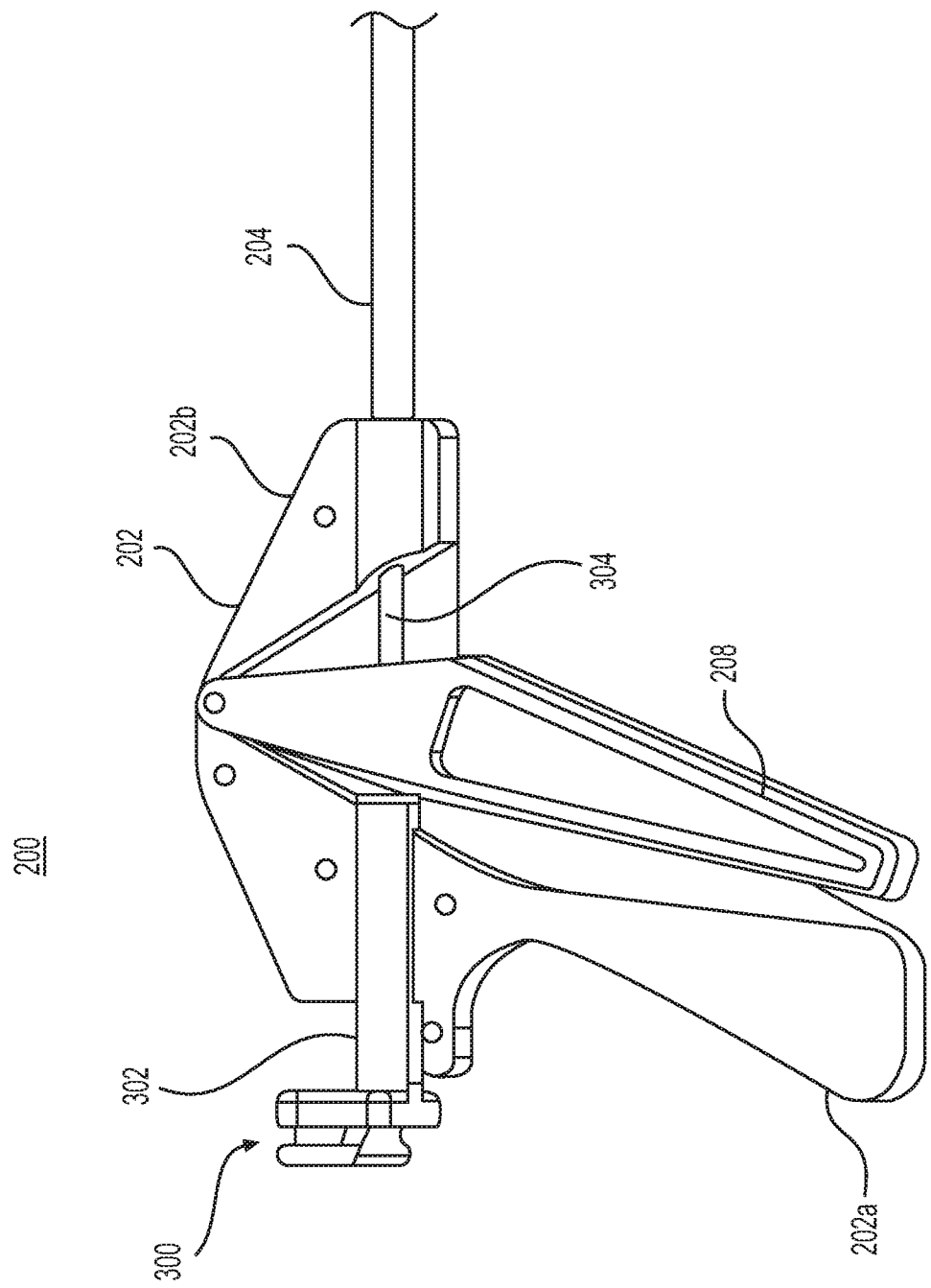
FIG. 3 illustrates the suture anchor delivery device illustrated with a cover thereof removed.

FIG. 3 illustrates an enlarged version of the suture anchor delivery device 200 illustrated in FIG. 2 with a cover thereof removed to more clearly illustrate individual components of the delivery device 200. The delivery device includes a trigger 208, which is pivotably mounted to the housing portion 202. The trigger 208 is configured to receive a squeezing force from a user of the delivery device 200 to move the trigger 208 from a first position to a second position in which the delivery device 200 is actuated, with respect to a fixed handle 202a. The elongate, tubular shaft 204 extends from a front end 202b of the housing portion 202. The housing portion 202, the shaft 204 and the trigger 208 make up a handle assembly of the delivery device.

Furthermore, the delivery device includes a draw bar assembly 300 mounted at a rear side of the housing portion 202 adjacent the handle 202a, which is opposite to the front end 202b of the housing portion 202 from which the shaft 204 extends. The draw bar assembly 300 includes a draw bar housing 302 and a draw bar tube 304 extending from the draw bar housing 302, through the housing portion 202 and through the shaft 204. The draw bar tube 304 is a hollow, tubular-shaped member. The draw bar assembly 300 also includes a draw bar 305 disposed within the draw bar tube 304. As is shown in FIG. 2, a tip of the draw bar 305, in an initial pre-deployment position of the delivery device 200, extends outward from the shaft tip 206. The draw bar 305 is configured to receive and support a suture anchor 100 mounted thereon.

Figure 4:
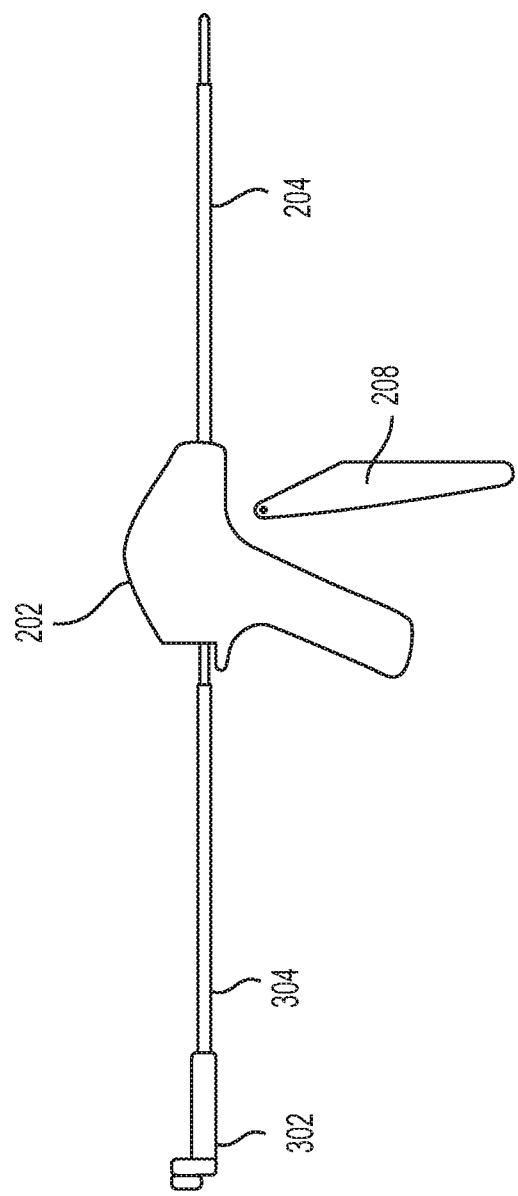
FIG. 4 illustrates an exploded view of the suture anchor delivery device.

FIG. 4 illustrates an exploded view of the delivery device 200 as illustrated in FIG. 3. The individual components discussed with respect to FIG. 3 are more clearly illustrated in the exploded view of FIG. 4.

Figure 5:
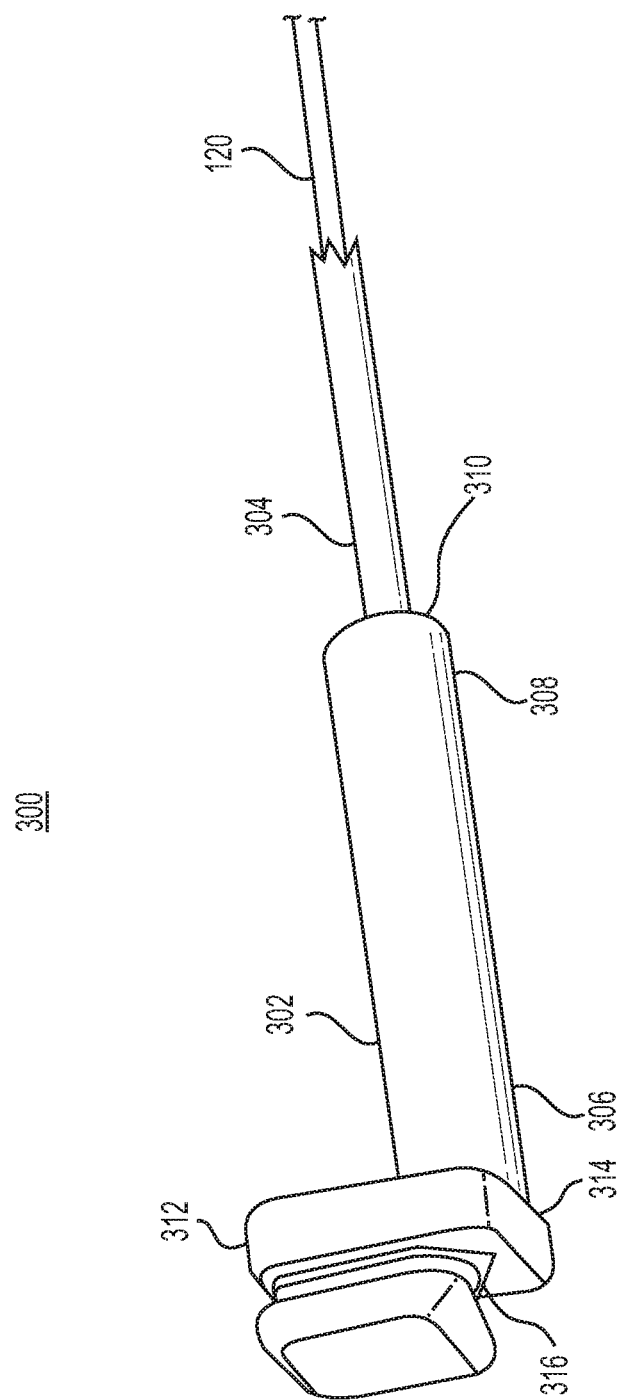
FIG. 5 illustrates a drive rod assembly 300 of the suture anchor delivery device.

FIG. 5 illustrates the draw bar assembly 300 in further detail. The draw bar housing 302 is a generally column-shaped member having the draw bar tube 304 extending outwardly therefrom. The draw bar assembly 300 is moveably mounted within the housing portion 202 of the delivery device such that the draw bar assembly 300 is linearly retractable from its initial position (see FIG. 3 described above) in the housing portion 202. An elongated flat portion 306 extends along a bottom of the draw bar housing 302. The flat portion 306 is provided for orientation of the draw bar housing 302 within the housing portion 202. Furthermore, a locking tab 308 is disposed along the bottom of the draw bar housing 302 at an end 310 of the draw bar housing 302 from which the draw bar tube 304 extends. The locking tab 308 acts as a stop and prevents full withdrawal of the draw bar assembly 300 from the housing portion 202. A vertically disposed flange portion 312 is disposed at a rear end 314 of the draw bar housing 302. An undercut portion 316 is formed within the flange portion 312. The undercut portion 316 is configured to receive an end of the at least one suture 120. The at least one suture 120 extends through the draw bar tube 304, through draw bar housing 304 and is then wrapped around the undercut portion 312. If necessary, an optional O-ring may be used to hold the at least one suture 120 in place around the undercut portion 316.

Figure 6:
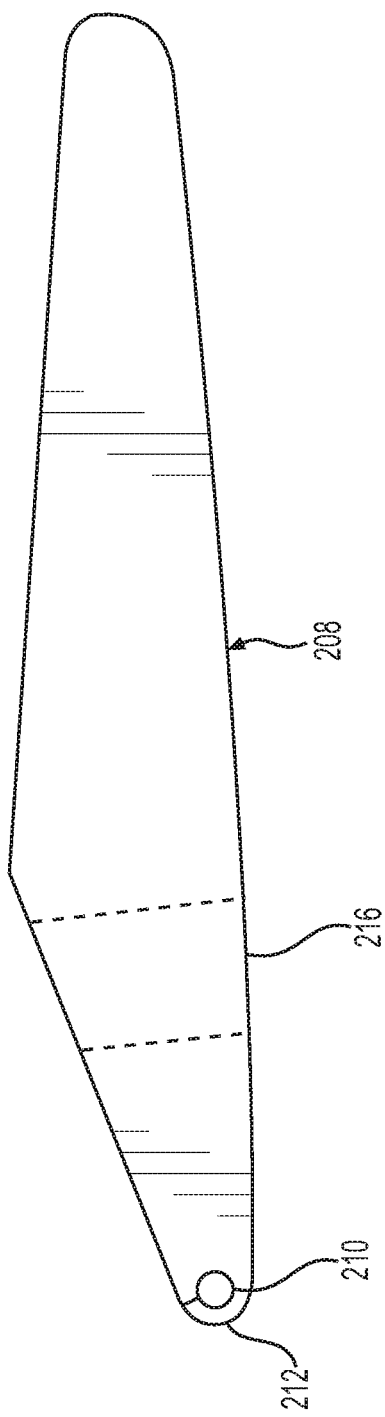
FIG. 6 illustrates a trigger 208 of the suture anchor delivery device.

FIG. 6 illustrates the trigger 208 of the delivery device 200. The trigger 208 includes a pivot hole 210 through a top end 212 of the trigger 208. The pivot hole 210 is configured to receive a pivot pin 214 (see FIG. 7) to pivotably mount the trigger 208 to the housing portion 202. The trigger 208 also includes a cutout 216 extending longitudinally through the trigger 208. The cutout 216 is configured to receive the draw bar tube 304, such that the draw bar tube 304 passes through the trigger 208.

Figure 7:
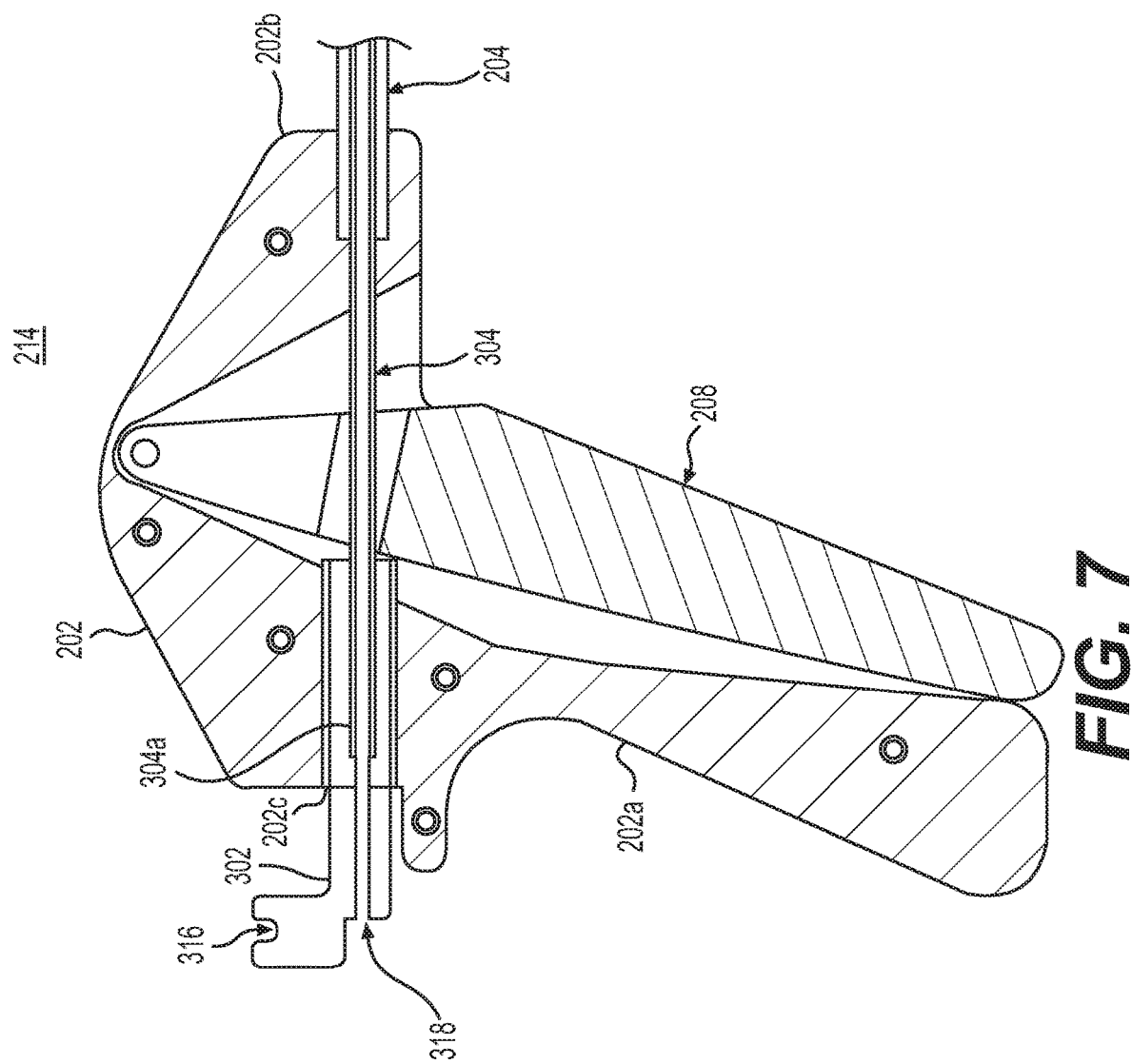
FIG. 7 illustrates a cross sectional view of the housing portion 202 of the suture anchor delivery device.

FIG. 7 illustrates a cross sectional view of the housing portion 202 of the suture anchor delivery device 200. As discussed above, the trigger 208 is pivotably attached to the housing portion 202 by the pivot pin 214. The draw bar assembly 300 extends through an opening 202a in the housing portion 202. The trigger 208 is movable with respect to the fixed handle 202a. The draw bar housing 302 extends through the handle 202a. A first end 304a of the draw bar tube 304 is mounted within the draw bar housing 302. The draw bar tube 304 extends out from the end 310 of the draw bar housing 302 and extends through the cutout 216 into the shaft 204, which is mounted within a front end 202b of the housing portion 202. The draw bar housing 302 has a suture thru channel 318 disposed therethrough. The at least one suture 120 extends through the channel 318 and is then wound around the undercut portion 316. When the trigger 208 is squeezed, a force is applied against the draw bar housing 302 to push the draw bar assembly 300 back through the opening 202c of the housing portion 202. As the draw bar assembly 300 is actuated the draw bar 305 is pulled back through the shaft tip 206. With the draw bar 305, the at least one suture 120, which is wrapped around the cut out portion 316 is also pulled back. The stop 308 prevents the draw bar assembly 300 from being removed entirely from the housing portion 202.

Figure 8:
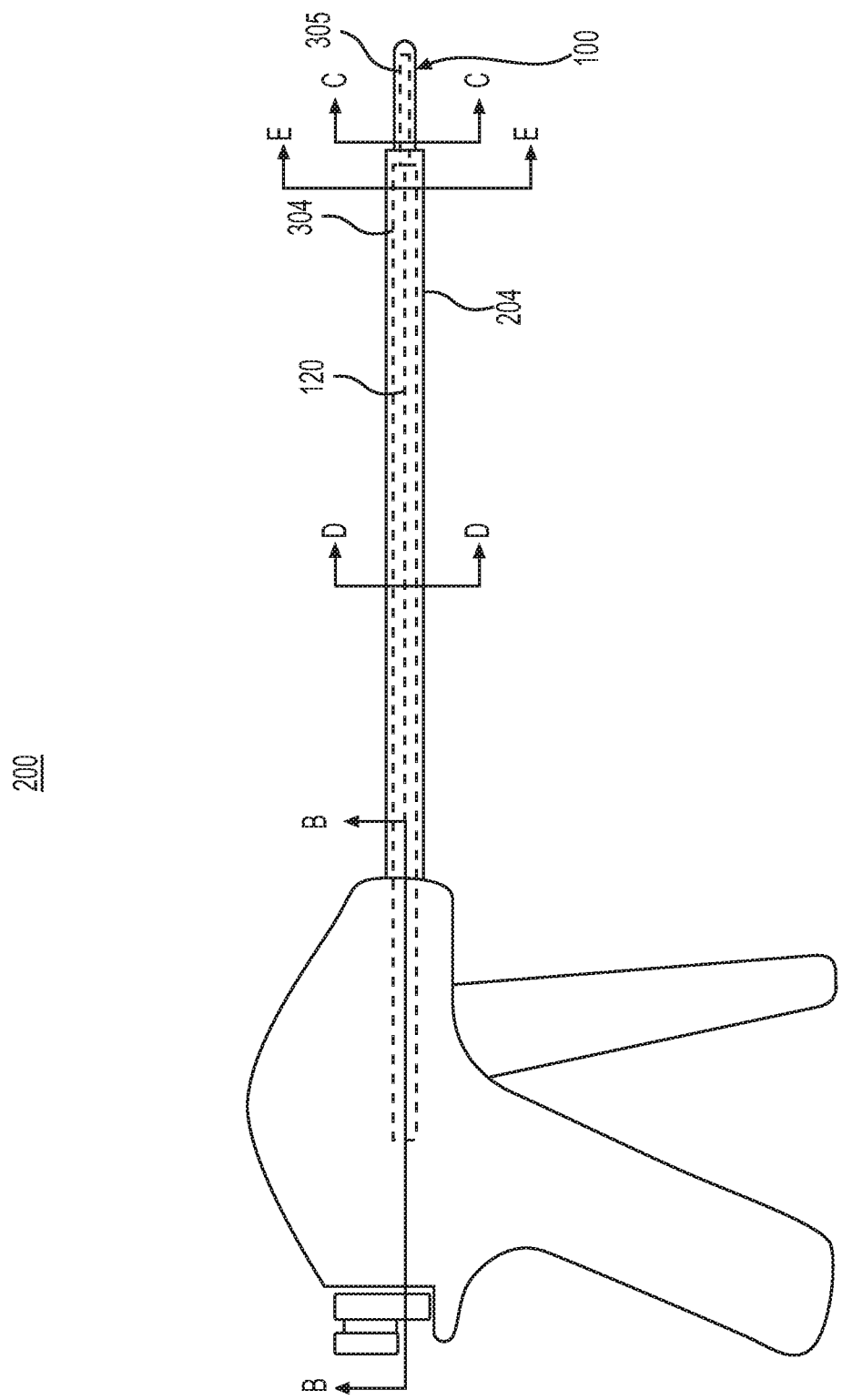
FIG. 8 illustrates the delivery device 200 with the anchor 100 mounted thereon.

FIG. 8 illustrates the delivery device 200 with the anchor 100 mounted on the end of the draw bar 305. The delivery device 200 and anchor are illustrated in FIG. 8 in the initial position prior to the deployment of the anchor 100.

Figure 9:
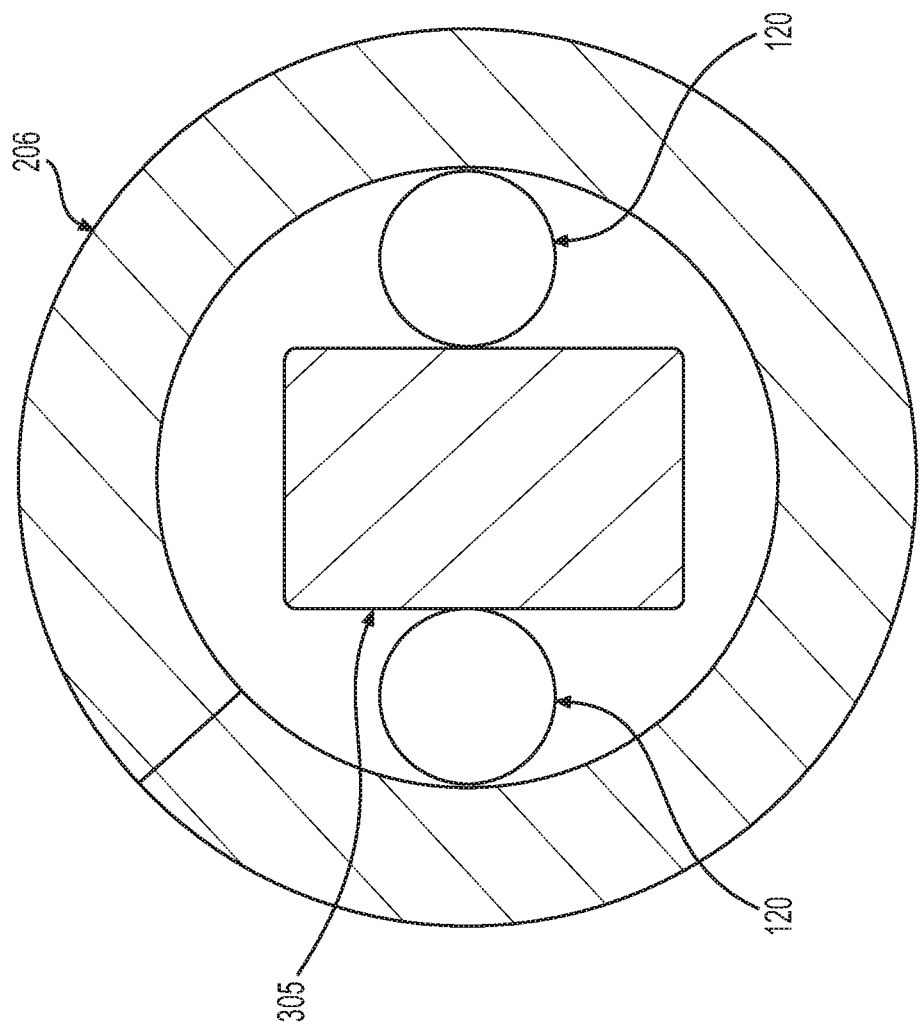
FIG. 9 illustrates a cross sectional view of an end of the suture anchor delivery device along section CC from FIG. 8.
Figure 10:
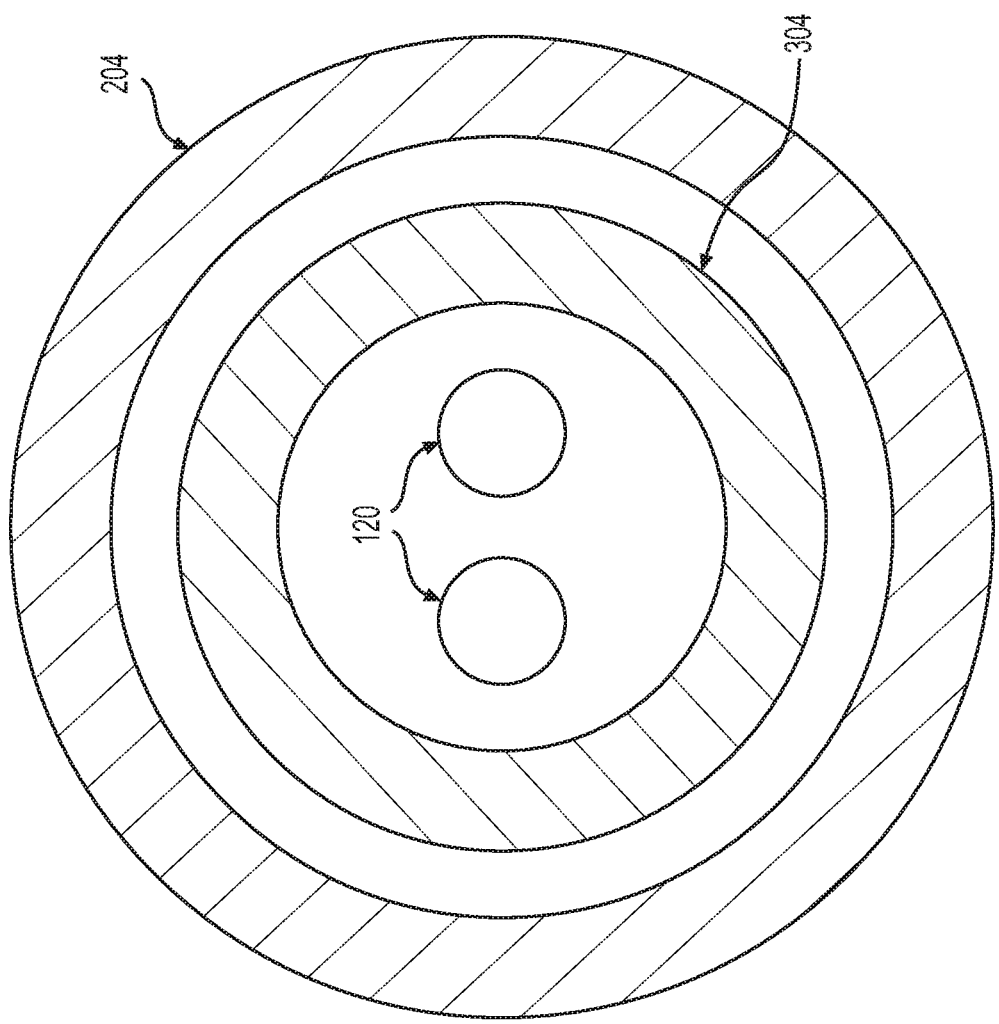
FIG. 10 is a cross sectional view of the delivery device along section DD in FIG. 8.
Figure 11:
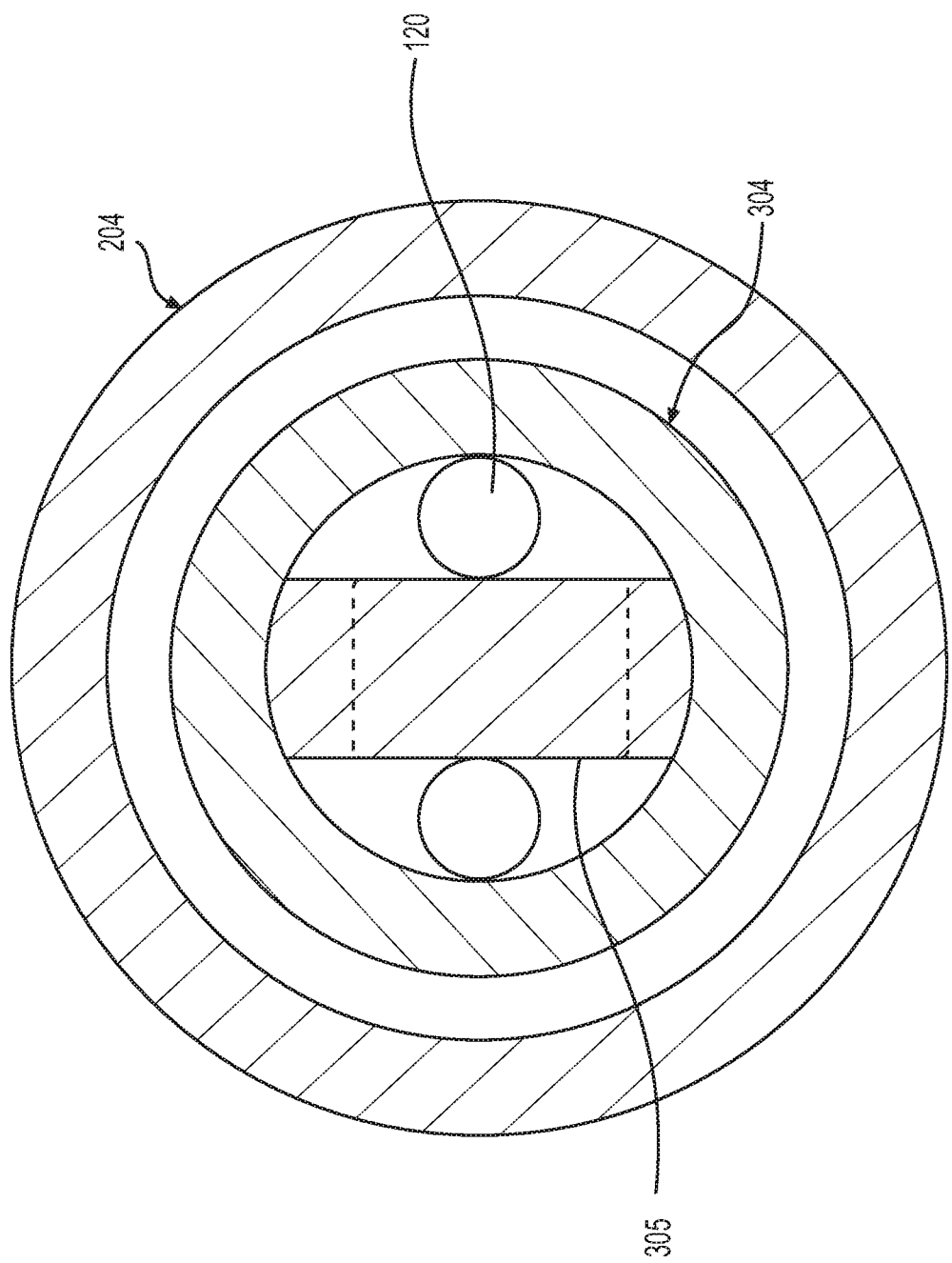
FIG. 11 is a cross sectional view of the delivery device along section EE in FIG. 8.

FIG. 9 is a cross sectional view of the delivery device along section CC in FIG. 8. The suture 120 is disposed within the shaft tip 206. The draw bar 305 of the draw bar tube 304 is disposed between the two ends of the suture 120. Extra space is provided within the shaft tip 206 in the event additional sutures are provided. Furthermore, FIG. 10 is a cross sectional view of the delivery device along section DD in FIG. 8. The at least one suture 120 extends through the draw bar tube 304, which extends through the tubular shaft 204. Still further, FIG. 11 is a cross sectional view of the delivery device along section EE in FIG. 8. The at least one suture 120 and the draw bar 305 extend through the draw bar tube 304.

Figure 12:
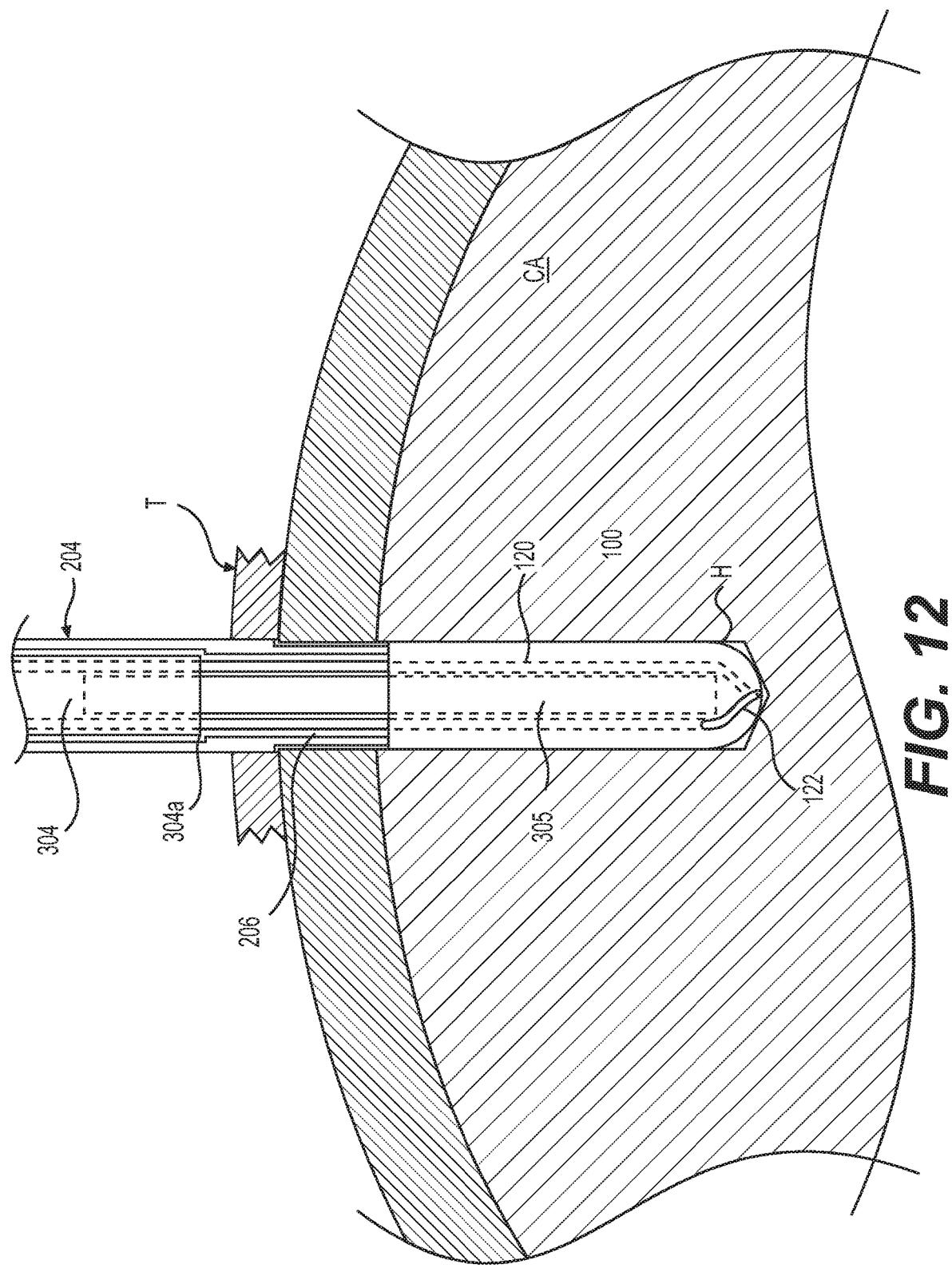
FIG. 12 illustrates the suture anchor delivery device and suture anchor inserted in a bone prior to deployment.

FIG. 12 illustrates the suture anchor delivery device 200 and suture anchor 100 inserted in a bone prior to deployment. During use, a hole H is drilled into the patient's bone. The delivery device 200, with the anchor 100 mounted thereon, are inserted through the hole through a patient's tissue T, through an outer layer of cortical bone CO and then into an inner layer of cancellous bone CA. The at least one suture 120 is woven through the anchor 100. As is illustrated in FIG. 12, the draw bar 305 is positioned at an end 304a of the draw bar tube 304 and extends outwardly therefrom through the shaft tip 206. The draw bar 305 extends outwardly from the shaft tip 206 and the anchor 100 is mounted on the draw bar 305. According to an exemplary aspect of the invention, the draw bar 305 is integrally formed with the draw bar tube 304.

Figure 13:
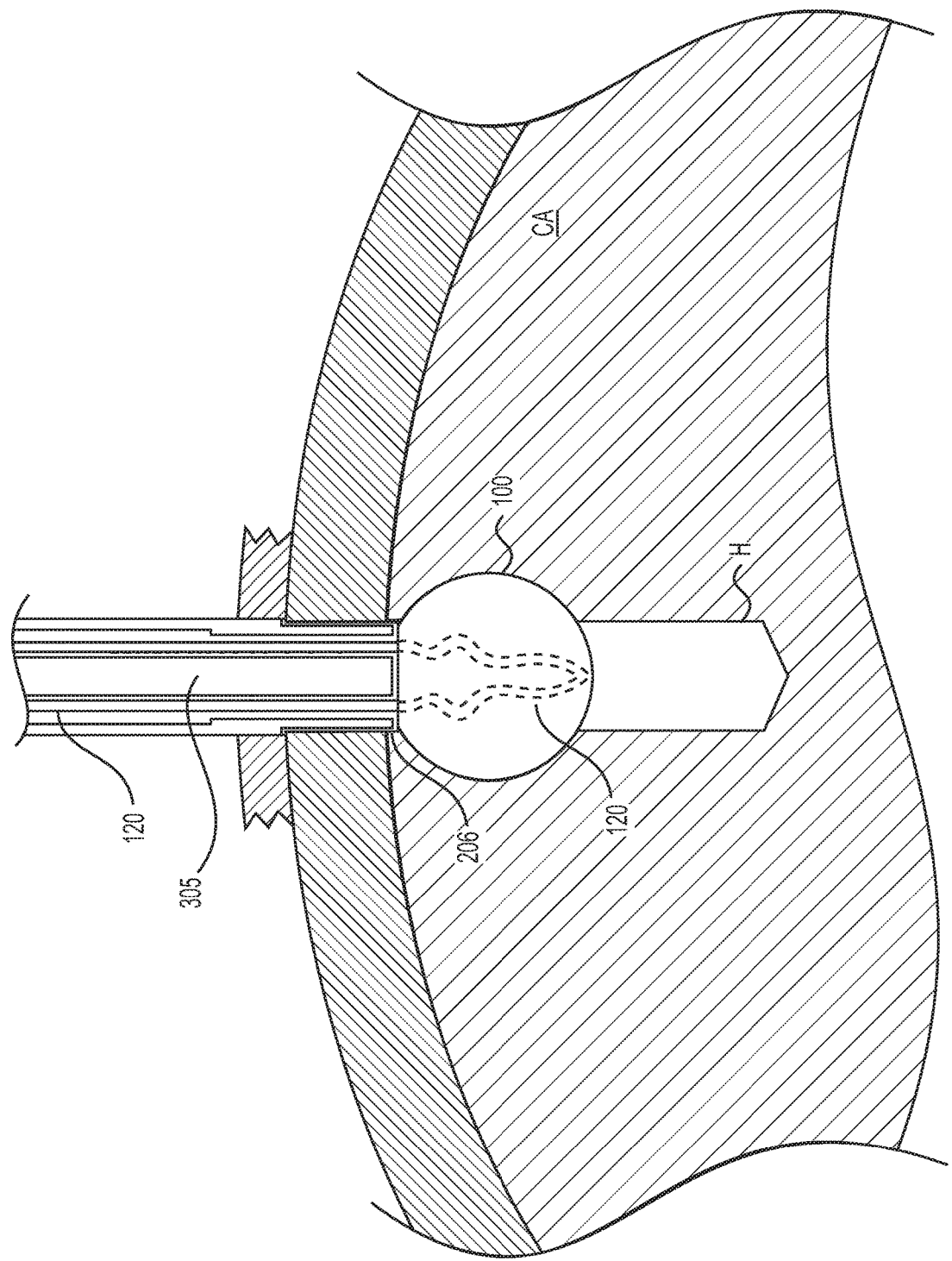
FIG. 13 illustrates the suture anchor delivery device and suture anchor inserted in a bone after deployment.

FIG. 13 illustrates the suture anchor delivery device 200 and suture anchor 100 inserted in the bone after deployment. Once the delivery device 200 is actuated, the anchor 100 is pulled up by the at least one suture 120 and is collapsed. As the anchor 100 collapses it compresses into the side of the bone CA creating a ball-like shape. The draw bar 305 is retracted at the same time the suture 120 is retracted by the draw bar assembly 300. The shaft tip 206 prevents the anchor 100 from coming out of the bone CA during the process.

When the trigger 208 is squeezed, a force is applied against the draw bar housing 302 to push the draw bar assembly 300 back through the opening 202c of the housing portion 202. As the draw bar assembly 300 is actuated the draw bar 305 is pulled back through the shaft tip 206. With the draw bar 305, the at least one suture 120, which is wrapped around the cut out portion 316 is also pulled back. The pulling back of the at least one suture 120 collapses the anchor 100.

Figure 14:
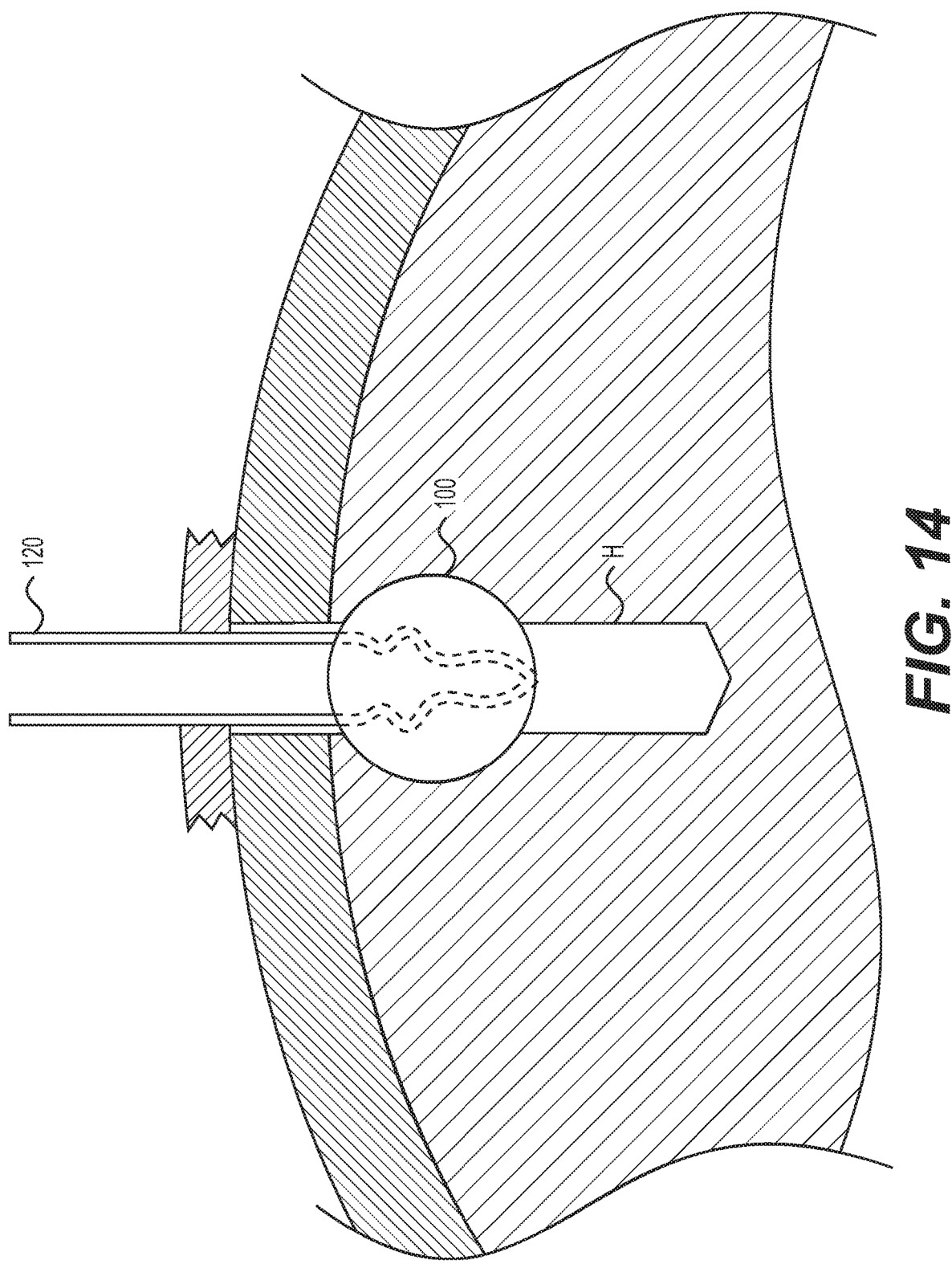
FIG. 14 illustrates the suture anchor and suture having been fixed in the tissue.

FIG. 14 illustrates the suture anchor 100 and suture 120 having been fixed in the tissue. In FIG. 14, the delivery device 200 is removed from the hole H, leaving only the anchor 100 and the suture 120. Once the delivery device 200 is fully deployed with the anchor 100 in the drill hole H, the suture 120 is released (i.e., unraveled) from the draw bar assembly 300. The delivery device 200 is then removed from the hole H and the suture 120 is removed from the delivery device. The suture 120 is then tightened and knotted to close the tissue. With the claimed invention, since the anchor 100 itself is made entirely of suture material, only suture material remains in the bone and tissue.

As detailed above, the locking knot 124 prevents the suture(s) from relaxing, which would cause the device to straighten, particularly following the deployment phase and before the suture is knotted to close the tissue. The only way to otherwise prevent this would be to apply constant tension to the suture during this interim period, which could last several minutes if not longer. Thus, the feature of the locking knot is important for maintaining the stability of the device after deployment.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A suture anchor delivery device, comprising:
  a handle assembly, comprising:
    a handle portion;
    a trigger, pivotably attached to the handle portion; and
    a tubular shaft extending through the handle assembly; and
  a draw bar assembly retractably disposed within the handle assembly, the draw bar assembly comprising:
    a draw bar tube extending through the tubular shaft, the draw bar tube having a channel disposed through the draw bar tube configured to receive a suture;
    a draw bar housing disposed at a first end of the tubular shaft, the draw bar housing having a cutout configured to receive an end of the suture such that the end of the suture wraps around the cutout; and
    a draw bar disposed within the draw bar tube and configured to receive a suture anchor mounted on a tip of the draw bar,
    wherein upon actuating the trigger the entire draw bar assembly is retracted.

2. The suture anchor delivery device according to claim 1, wherein the draw bar assembly further comprises a flat portion extending along a bottom of the draw bar housing for orienting the draw bar housing within the handle portion.

3. The suture anchor delivery device according to claim 1, wherein the draw bar assembly further comprises a stop member configured to prevent the draw bar assembly from being completely removed from the handle portion.

4. A suture delivery system, comprising:
  a suture anchor having a tubular anchor body made of suture material, the tubular anchor body having a distal tip and a bore extending through the tubular anchor body to a proximal end of the tubular anchor body;
  a suture woven from the distal tip and extending through the bore and exiting through the proximal end; and
  a delivery device, comprising:
    a handle assembly, comprising:
      a handle portion;
      a trigger, pivotably attached to the handle portion; and
      a tubular shaft extending through the handle assembly;
    a draw bar assembly retractably disposed within the handle assembly, the draw bar assembly comprising:
      a draw bar tube extending through the tubular shaft, the draw bar tube having a channel disposed through the draw bar tube configured to receive the suture;
      a draw bar housing disposed at a first end of the tubular shaft, the draw bar housing having a cutout configured to receive an end of the suture such that the end of the suture wraps around the cutout; and
      a draw bar disposed within the draw bar tube and configured to receive the suture anchor mounted on a tip of the draw bar,
    wherein upon actuating the trigger the entire draw bar assembly is retracted.

5. The suture delivery system according to claim 4, wherein the tubular anchor body is configured such that pulling an end of the suture at the proximal end causes the tubular anchor body to become compressed.

6. The suture delivery system according to claim 4, wherein the tubular anchor body is made entirely of suture material.

7. The suture delivery system according to claim 4, wherein the tubular anchor body consists of suture material.

8. The suture delivery system according to claim 4, wherein an entirety of the suture anchor is made of only suture material.

9. The suture delivery system according to claim 4, wherein the suture forms a suture loop outside of the distal tip.

10. The suture delivery system according to claim 4, wherein a plurality of sutures is woven from the distal tip and extending through the bore and exiting through the proximal end.

11. The suture delivery system according to claim 10, wherein each of the plurality of sutures forms a suture loop outside of the distal tip.

12. The suture delivery system according to claim 4, wherein the suture anchor consists of:
  the tubular anchor body made of entirely of suture material; and
  the suture.

* * * * *